(12) United States Patent
Falahee

(10) Patent No.: US 7,488,315 B2
(45) Date of Patent: Feb. 10, 2009

(54) SURGICAL SMOKE FIELD EVACUATORS

(75) Inventor: Mark H. Falahee, Ann Arbor, MI (US)

(73) Assignee: Medical Designs, LLC, Ann Arbor, MI (US)

( * ) Notice: Subject to any disclaimer, the term of this patent is extended or adjusted under 35 U.S.C. 154(b) by 514 days.

(21) Appl. No.: 10/935,213

(22) Filed: Sep. 7, 2004

(65) Prior Publication Data

US 2005/0054993 A1 Mar. 10, 2005

Related U.S. Application Data

(60) Provisional application No. 60/500,636, filed on Sep. 5, 2003, provisional application No. 60/501,046, filed on Sep. 8, 2003.

(51) Int. Cl.
*A61M 1/00* (2006.01)

(52) U.S. Cl. ...................................... 604/540

(58) Field of Classification Search ......... 604/313–316, 604/540, 317; 55/342; 273/286
See application file for complete search history.

(56) References Cited

U.S. PATENT DOCUMENTS

| | | | |
|---|---|---|---|
| 4,182,641 A | 1/1980 | Fitts | 156/77 |
| 4,308,308 A | 12/1981 | Sachse | 428/168 |
| 4,448,832 A | 5/1984 | Kidwell | 428/113 |
| 4,612,748 A | 9/1986 | Arnold et al. | 52/309.16 |
| 5,015,243 A * | 5/1991 | Schifano | 604/315 |
| 5,305,568 A | 4/1994 | Beckerman | 52/309.4 |
| 5,322,521 A * | 6/1994 | Wilk | 604/317 |
| 5,364,491 A | 11/1994 | Aochi et al. | 156/446 |
| 5,742,992 A | 4/1998 | Kaempen | 29/455.1 |
| 5,941,873 A * | 8/1999 | Korenfeld | 606/1 |
| 6,186,966 B1 | 2/2001 | Grim et al. | 602/6 |
| 6,447,886 B1 | 9/2002 | Mohamed et al. | 428/209 |
| 6,451,241 B1 | 9/2002 | Ohliger et al. | 264/510 |
| 6,504,985 B2 * | 1/2003 | Parker et al. | 385/133 |
| 6,524,980 B1 | 2/2003 | Fensel et al. | 442/181 |
| 6,663,610 B1 * | 12/2003 | Thompson et al. | 604/313 |
| RE38,508 E | 4/2004 | Wright | 428/623 |
| 6,740,381 B2 | 5/2004 | Day et al. | 428/56 |
| 7,141,047 B2 * | 11/2006 | John | 604/541 |

* cited by examiner

*Primary Examiner*—Michele Kidwell
(74) *Attorney, Agent, or Firm*—Gifford, Krass, Sprinkle, Anderson & Citkowski, P.C.

(57) ABSTRACT

Universally adaptable evacuators are adaptable to all surgical fields, easy to apply and, in most cases, may be expanded and/or removed as necessary. A hollow tube including a fitting adapted for connection to a vacuum source and at least one smoke inlet is held in position with the smoke inlet proximate to a surgical wound. According to a preferred embodiment, a stapling tab extending from a flexible perforated tube is used to hold the evacuator in place around the periphery of a surgical incision. According to an alternative embodiment, a smoke evacuator attaches temporarily or permanently to a retractor or other surgical instrument. Standard tubing and couplers may be used and the assembly may be prepackaged in sterile condition and disposed after use.

4 Claims, 3 Drawing Sheets

025B
SURGICAL SMOKE FIELD EVACUATORS

REFERENCE TO RELATED APPLICATION

This application claims priority from U.S. Provisional Patent Application Ser. No. 60/500,636, filed Sep. 5, 2003, and Ser. No. 60/501,046, filed Sep. 8, 2003, the entire content of both applications being incorporated herein by reference.

FIELD OF THE INVENTION

This invention relates generally to surgical smoke evacuators and, in particular, to universally adaptable smoke evacuators applicable to numerous surgical wound types and locations.

BACKGROUND OF THE INVENTION

Modern surgical techniques typically utilize a "bovie" and/or bipolar cauterizing systems which can generate considerable amounts of smoke. This smoke often clouds the operative field of sight, and is potentially hazardous to attending personnel.

Smoke evacuation attached directly to operating bovie effectively eliminates smoke, but blocks the surgical view and makes use of the bovie cumbersome. Large hose evacuators placed near the operative incision are loud, in the way, and do not effectively or rapidly remove smoke from all fields.

SUMMARY OF THE INVENTION

This invention resides in universally adaptable evacuators used to eliminate smoke from an operative site, regardless of surgical wound type or location. The devices described herein are adaptable to all surgical fields, easy to apply and, in most cases, may be expanded and/or removed as necessary. They are also inexpensive, work with existing operating room suction systems, and they are quiet. They require no attachment to other surgical tools other than a vacuum source and, being low profile, are out of operative line of sight.

A surgical field smoke evacuator according to the invention comprises a hollow, flexible tube including a fitting adapted for connection to a vacuum source and at least one smoke inlet. At least one element is provided for holding the tube in position with the smoke inlet proximate to a surgical wound.

According to a preferred embodiment, the element is a stapling tab extending from a hollow, flexible perforated tube. According to an alternative embodiment, a smoke evacuator attaches temporarily or permanently to a retractor or other surgical instrument. Standard tubing and couplers may be used and the assembly may be prepackaged in sterile condition and disposed after use.

DETAILED DESCRIPTION OF THE INVENTION

Figure 1:
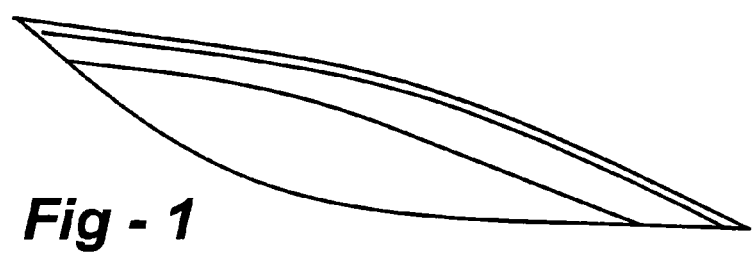
FIG. 1 is a drawing of a typical incision, showing the opposing borders.

Turning now to the drawings, FIG. 1 shows a typical surgical incision, which includes pointed ends and curved sidewalls.

Figure 2:
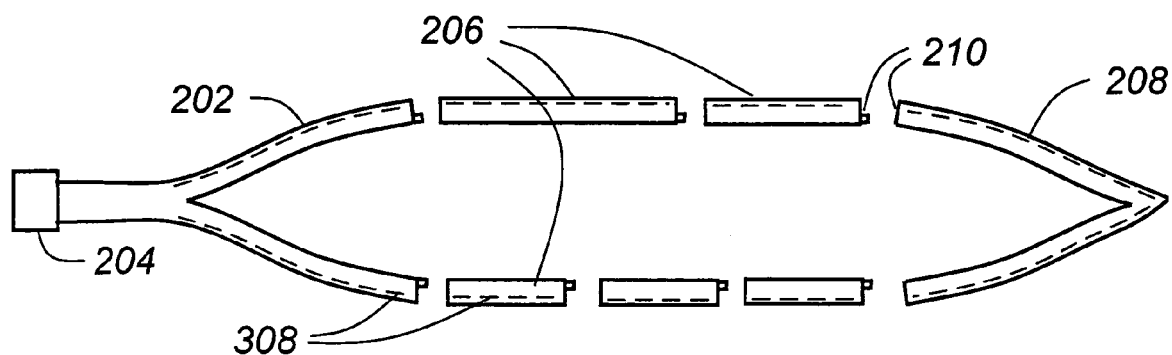
FIG. 2 is a drawing of a preferred, modular smoke evacuation assembly according to the invention.

FIG. 2 is a drawing which shows a modular smoke evacuation system according to the invention. This system comprises a suction end piece 202 having a connector 204 adapted for interconnection to a standard suction system, and varying length expander pieces 206 and an end connector 208. Between each piece, there is a coupling interconnect represented by 210, allowing the various components to be assembled to correspond to the incision, for example, of the type shown in FIG. 1.

Figure 3:
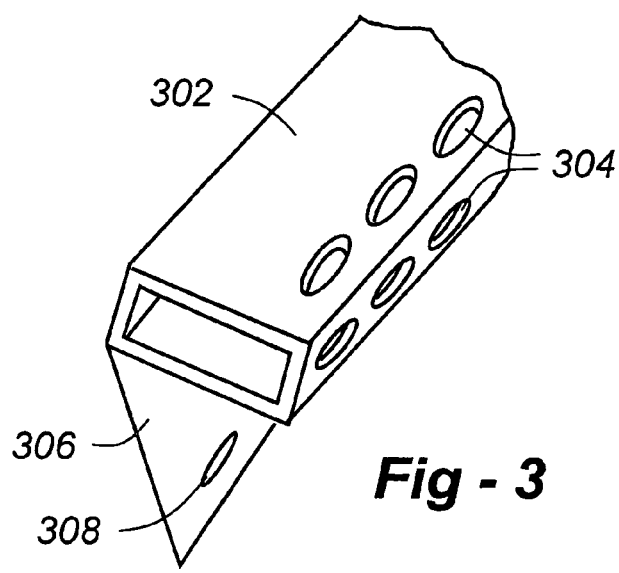
FIG. 3 is a close-up view drawing of the suction system, showing evacuation holes and anchor points.

FIG. 3 is an end-view drawing of one of the pieces 202, 206, 208, which generally has a hollow body 302 to evacuate smoke through ports 304, as well as a lengthwise tab 306, preferably including apertures 308 to assist with stapling. The angle between the tubing portion 302 and the tab 306 is preferably on the order of 45 to 60 degrees, though it should be recognized that other angles are possible, including no angle at all; that is, with the stapling tab 306 and body 302 may form a generally flattened structure.

Figure 4:
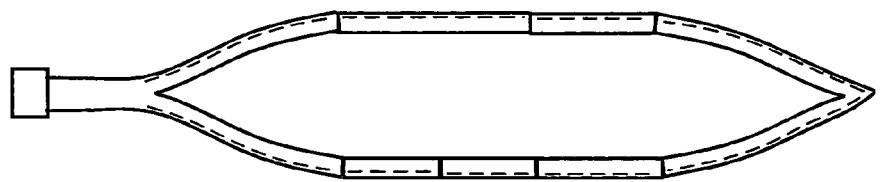
FIG. 4 is a drawing that shows the assembly of FIG. 2 interconnected.

Although apertures 308 are divided to assist with stapling, at least the material of 306 may be sufficiently penetratable that staples may go right through it without the need for separate perforations. Also, although apertures 304 are shown on two sides of body 302, they may be located in a single row, and the structure 302 need not be rectangular in cross section, but may be circular, oval, or other shape. FIG. 4 is a drawing which shows the modular assembly of FIG. 2 interconnected, with the connections 210 making a smoke-communicating path to the coupler 204.

Figure 5:
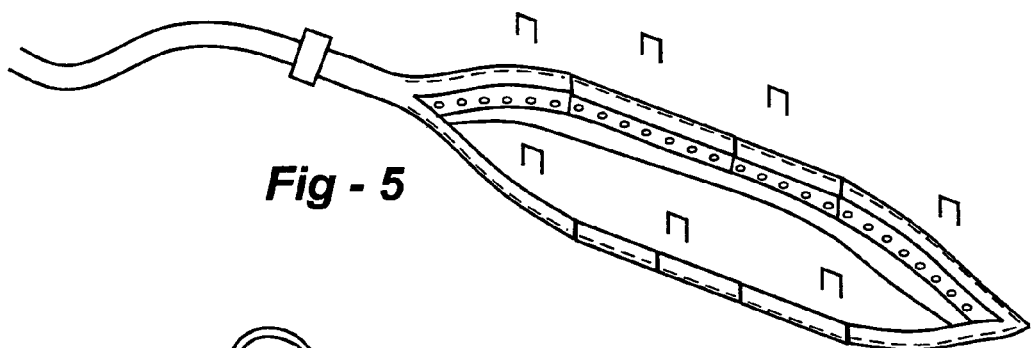
FIG. 5 shows the interconnected assembly being stapled into place.
Figure 6:
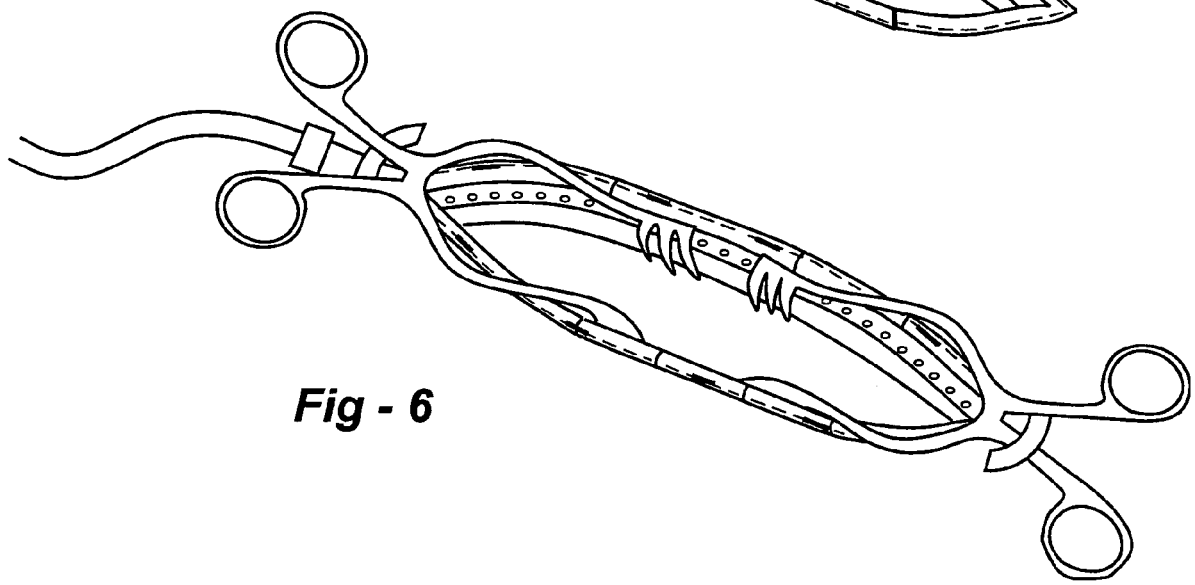
FIG. 6 shows the way in which the modular embodiment is compatible with standard retractors.

In terms of surgical procedure, the physician proceeds with the usual preparation and drape, placing a standard suction hose on the operative field. An incision is made down through subcutaneous tissue to deep fascia, with bleeding tissues being cauterized as necessary. The suction system is assembled, as shown in FIG. 4, and placed down along the wound edges, as shown in FIG. 5. The assembled device is stapled down, and a hose to the suction system is attached as shown. As shown in FIG. 6, one advantage of the invention is that it is fully compatible with retractor systems, particularly with the various lengths of the side tubes being provided in different geometries so that the overall arrangement may be configured as desired.

Figure 7:
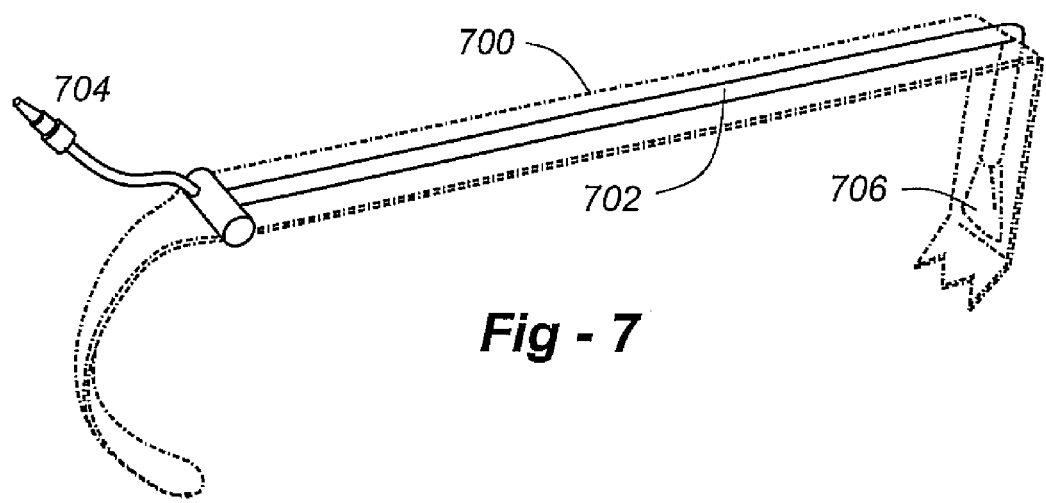
FIG. 7 is a drawing of an alternative embodiment of the invention attached to a Hibbs-type retractor.

FIG. 7 is a drawing that shows an alternative embodiment of the invention, wherein a smoke evacuator attaches directly to a retractor. In this case, a Hibbs-type retractor 700 is shown, with the suction tube 702, standard tapered coupling 704, and a flared end 706. The tube 702 may be metal, in which case it may be welded or otherwise permanently attached to the retractor, sterilized and re-used. Although a Hibbs-type retractor is shown, it will be appreciated by those of skill in the art that the "permanent" type of arrangement depicted in FIG. 7 is applicable to other types of retractors.

Figure 8:
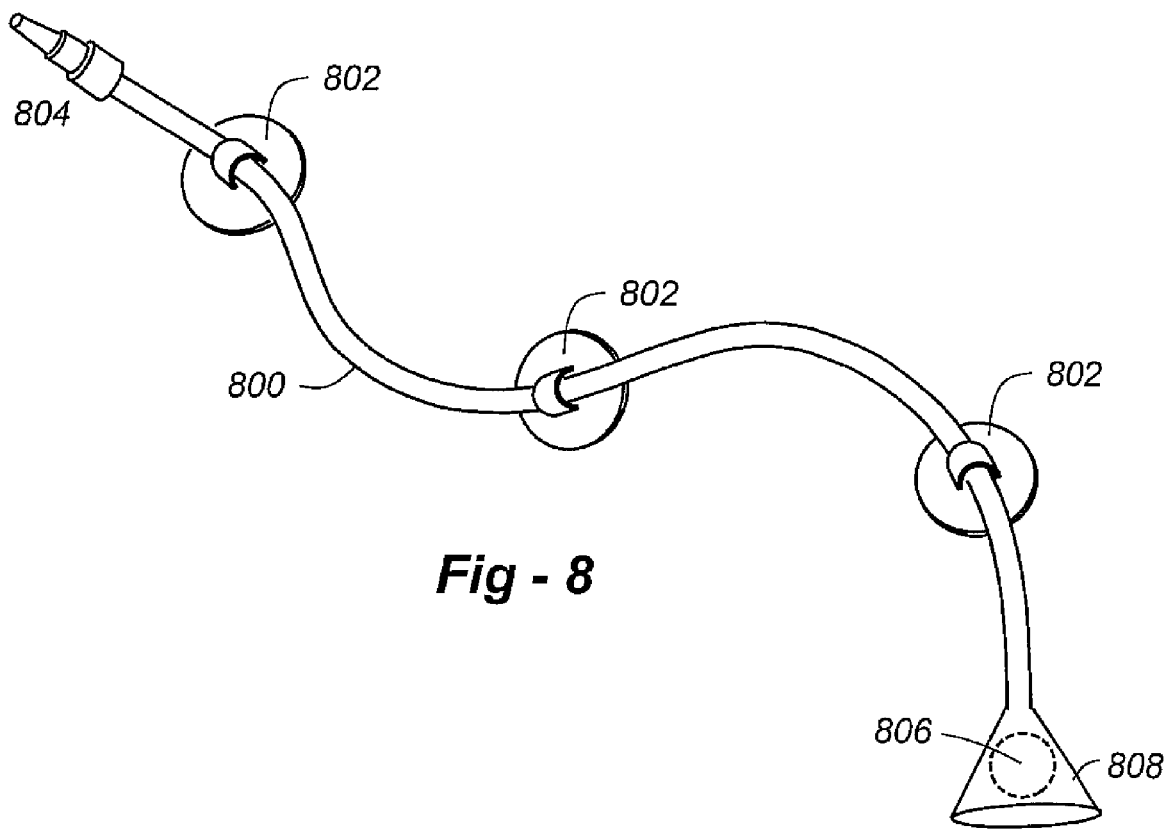
FIG. 8 is a drawing which shows a further embodiment of the invention in the form of a disposable, transferable smoke evacuator with modular attachment points.

As an alternative to a permanent attachment, FIG. 8 illustrates a temporarily attachable, preferably disposable smoke evacuator, which is attached to a retractor utilizing snap-on/off attachments and hook-and-loop pads 802. This configuration comprises a flexible plastic tubing 800, having a proximal end 804 with a standard evacuator attachment, and a distal end 808, preferably including a flared intake area and hook-and-loop backing 806 or other type of fastener attachment. The pads may be slid or snapped to different points along the length of the tube 800, enabling the system to accommodate different types of retractors or other surgical instruments, as necessary, for smoke evacuation.

In terms of surgical procedure, the evacuator of FIG. 8 is attached to the retractor as convenient, with the distal end placed in close proximity to the smoke generation point, thereby eliminating smoke rapidly, keeping the field of view clear. Among the advantages of this embodiment is that the evacuator may be attached to any type of handheld or stationary retractors, and does not hamper the operative tools.

I claim:

1. A surgical field smoke evacuator, comprising:
   a hollow, flexible tube having a proximal end with a fitting adapted for connection to a vacuum source and a distal end that branches into a pair of side tubes, each side tube having a plurality of smoke inlets;
   the side tubes being composed of modular, interconnectable sections; and
   at least one element for holding the side tubes in position with the smoke inlets proximate to a surgical wound.

2. The surgical field smoke evacuator of claim 1, wherein the element is a stapling tab extending from the hollow, flexible tube.

3. The surgical field smoke evacuator of claim 1, wherein the side tubes rejoin distally after the branching.

4. The surgical field smoke evacuator of claim 1, wherein the modular, interconnectable sections are of varying lengths to accommodate different incision dimensions.

* * * * *